US010549000B2

(12) United States Patent
Yellen et al.

(10) Patent No.: US 10,549,000 B2
(45) Date of Patent: Feb. 4, 2020

(54) HANDHELD UV DISINFECTANT UNIT

(71) Applicant: Healthy Signoff, LLC, Scottsdale, AZ (US)

(72) Inventors: Iris Yellen, Bloomfield Hills, MI (US); Shelley Katz, Scottsdale, AZ (US); Mario Alexander Esquer, Scottsdale, AZ (US)

(73) Assignee: HEALTHY SIGNOFF, LLC, Scottsdale, AZ (US)

( * ) Notice: Subject to any disclaimer, the term of this patent is extended or adjusted under 35 U.S.C. 154(b) by 114 days.

(21) Appl. No.: 15/848,703

(22) Filed: Dec. 20, 2017

(65) Prior Publication Data

US 2019/0184044 A1 Jun. 20, 2019

(51) Int. Cl.
*A61L 2/10* (2006.01)

(52) U.S. Cl.
CPC ............ *A61L 2/10* (2013.01); *A61L 2202/11* (2013.01); *A61L 2202/16* (2013.01)

(58) Field of Classification Search
CPC ..... A61L 2/10; A61L 2202/11; A61L 2202/16
See application file for complete search history.

(56) References Cited

U.S. PATENT DOCUMENTS

| 7,888,657 | B1 | 2/2011 | Zadro |
| 8,168,963 | B2 | 5/2012 | Ratcliffe |
| 8,203,124 | B2 | 6/2012 | Havens et al. |
| 8,357,914 | B1 | 1/2013 | Caldwell |
| 9,256,302 | B2 | 2/2016 | Chang et al. |
| 9,265,849 | B2 | 2/2016 | Kerr |
| 9,339,576 | B2 | 5/2016 | LaPorte et al. |
| 9,572,901 | B2 | 2/2017 | Todeschini |
| 2004/0136180 | A1* | 7/2004 | Lewis ............... B43K 7/005 362/118 |
| 2008/0060153 | A1 | 3/2008 | Jansheski |
| 2011/0126370 | A1 | 6/2011 | Reuben |
| 2016/0331855 | A1 | 11/2016 | St. Louis et al. |
| 2017/0361639 | A1* | 12/2017 | Kaneda ............... B43K 27/006 |

OTHER PUBLICATIONS

Sid Perkins; This door handle kills germs; Science News for Students; May 27, 2015; pp. 1-4.
Radhika Seth; What a Sterile Door!; Dec. 16, 2010; pp. 1-5; www.yankodesign.com.

\* cited by examiner

*Primary Examiner* — Sean E Conley
(74) *Attorney, Agent, or Firm* — Brooks Kushman P.C.

(57) ABSTRACT

An ultraviolet (UV) light disinfectant unit is sized for portability and handheld use. The handheld UV light disinfectant unit includes a shell defining an interior cavity. A UV light is provided on an exterior of the shell. A transparent lens cap is provided over the UV light and is removably mounted to the shell. At least one writing instrument such as a pen and/or stylus is integrated into the handheld UV light disinfectant unit. The writing instrument is extendable away from the shell and retractable into the interior cavity. A slider button may be provided to slide the writing instrument between the retracted position and the extended position. A combination of a UV light and a writing instrument in a handheld device provides a user with a multiuse tool to accomplish tasks such as writing on publicly accessible screens that may make multiple steps of disinfecting desirable.

10 Claims, 4 Drawing Sheets

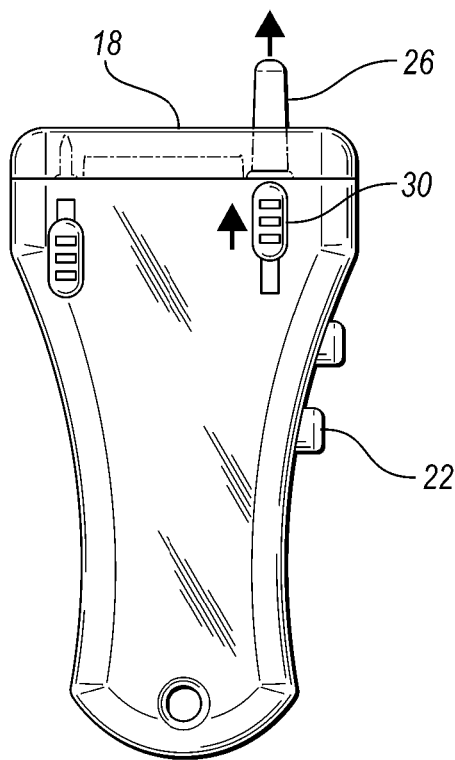
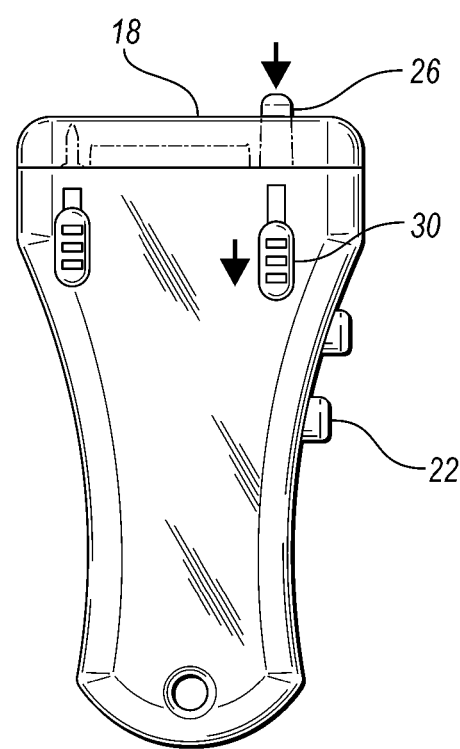
FIG. 2A          FIG. 2B
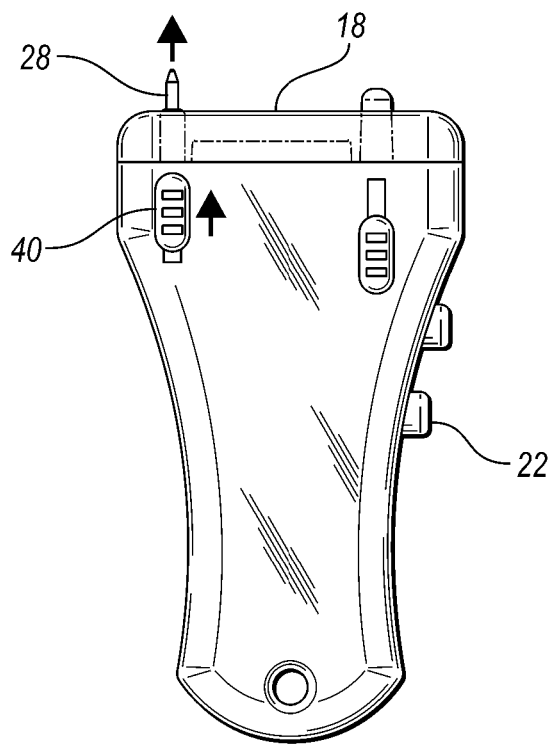
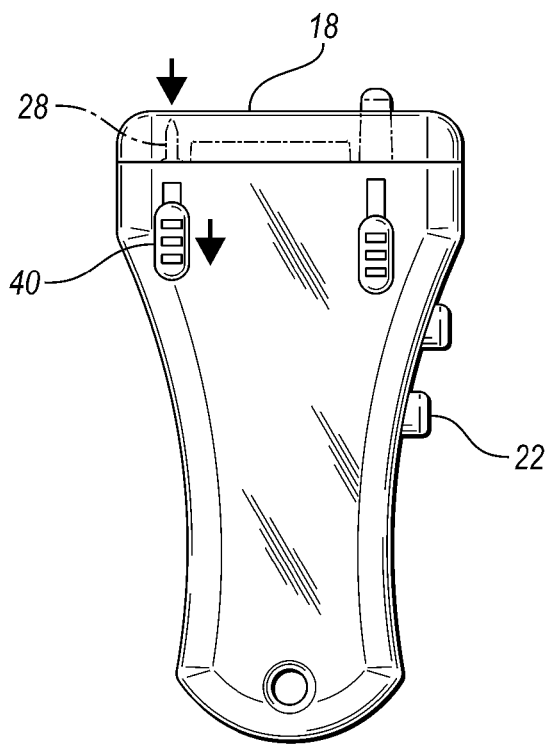
FIG. 3A          FIG. 3B

HANDHELD UV DISINFECTANT UNIT

TECHNICAL FIELD

This disclosure is generally directed to a handheld ultraviolet ("UV") disinfectant unit. More specifically, the handheld UV disinfectant unit has one or more writing instruments specially integrated into the unit, providing a handheld, convenient ability to disinfect a writing surface and subsequently write on the disinfected surface.

BACKGROUND

Ultraviolet (UV) light is a form of light that is invisible to the human eye. It resides on the electromagnetic spectrum between X-rays and visible light, having wavelengths roughly between 200 and 300 nanometers. One beneficial property of UV light is its ability to inactivate microorganisms, such as bacteria. When bacteria are exposed to UV light, they are rendered incapable of reproducing. This has led to a widespread adoption of UV light as a safe, effective disinfectant.

The market has seen recent attempts to capitalize on the disinfecting properties of UV light. For example, U.S. Pat. No. 8,357,914 discloses a disinfecting apparatus having a housing, a UV light, and a dispensing mechanism. The housing is designed to receive contaminated pens, immersing the pens in UV light, and then dispensing disinfected pens.

U.S. Pat. No. 9,339,576 discloses a personal electronic device (PED) sanitization device comprising a compartment configured to receive a plurality of PEDs and one or more emitters configured to emit electron-optical (EO) radiation, such as UV light, to disinfect the PED.

SUMMARY

According to one embodiment, a handheld UV light disinfectant unit includes a housing, and a UV light source coupled to the housing. The UV light source is configured to, when activated, disinfect a surface on which the UV light shines. A writing instruments is coupled to the housing.

The writing instrument may be a pen. The writing instrument may be a stylus. A second writing instrument may be coupled to the housing adjacent to the UV light source. The writing instrument may be a pen, while the second writing instrument may be a stylus. At least one of the pen or stylus may be configured to extend and retract through the housing. Both the pen and the stylus may be configured to extend and retract through the housing. At least one of the pen and stylus may be configured to extend and retract at a location adjacent the UV light source.

A transparent lens cap may be assembled over the UV light source to protect the light source. At least one of the writing instruments may be configured to extend and retract through the lens cap. The lens cap may be removably mounted to the housing.

A second UV light source may be mounted inside of the housing. At least a portion of the housing may be transparent to enable the UV light to transfer through the housing. The portion of the housing may be in a location where the user's hand is placed during operation of the handheld UV light disinfectant unit. The transparent portion of the housing may be in a grasping handle part of the unit.

The housing may have a first end, a second end, and a length extending between the ends. The UV light source may be mounted to or near the first end, and the housing may become smaller in a direction from the first end toward the second end.

According to another embodiment, a handheld UV light disinfectant unit includes a handheld housing defining a hollow interior having a first track and a second track therein. The housing further includes an end defining first and second apertures extending through the housing. A UV light source is mounted to or near the end and configured to, when activated, disinfect a surface on which UV light shines. A first slider extends through the housing and into the first track. The first slider is coupled to a pen to enable the pen to extend and retract through the first aperture as the first slider slides along the first track. A second slider extends through the housing and into the second track. The second slider is coupled to a stylus to enable the stylus to extend and retract through the second aperture as the second slider slides along the second track.

According to yet another embodiment, a handheld UV light disinfectant unit has a body having a first end, a second end, and a pair of sides connecting the ends defining a width of the unit therebetween. The unit is wider at the first end than at the second end. A UV light source is mounted to the first end. A writing instrument is configured to selectively extend and retract through the body.

BRIEF DESCRIPTION OF THE DRAWINGS

FIG. 2A is a top view of the handheld UV disinfectant unit of FIG. 1 with a stylus in an extended position, and FIG. 2B shows the stylus in a retracted position.

FIG. 3A is a top view of the handheld UV disinfectant unit of FIG. 1 with a pen in an extended position, and FIG. 3B shows the pen in a retracted position.

DETAILED DESCRIPTION

Figure 1:
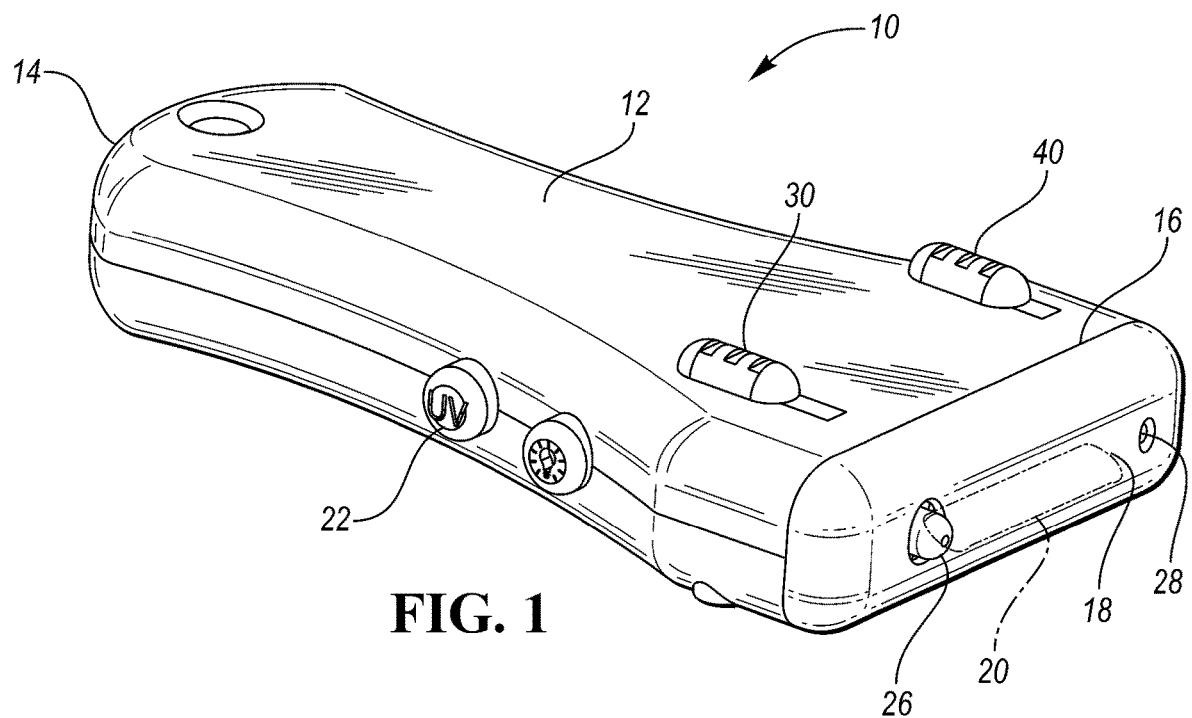
FIG. 1 is a perspective view of a handheld UV disinfectant unit, according to one embodiment.

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

As the knowledge level and concern over germs and bacteria increases, so does the need for disinfecting devices. As explained above, UV light has been used to disinfect surfaces of consumer goods (e.g., pens, personal electronic devices, etc.). However, the current UV light units are cumbersome and impractical for many every-day applications.

Germs and bacteria are present in all public fixtures and devices that require human interaction, especially with one's hands. This includes door handles, faucets, elevator buttons, hand rails, and countless others. It would be beneficial for an individual to have the ability to quickly and easily disinfect surfaces that will soon be purposefully touched by the individual. Once particular setting where such disinfection would be beneficial is credit card or payment user interfaces at the check-out lines at stores. These user interfaces typically include a scree requiring the purchaser to select payment options and sign their name to authorize and consent to payment. Months and years can go by without these surfaces being cleaned, after thousands and thousands of different individuals touching the screens with their hands. This leads to a region rife with bacteria and germs. Moreover, these user interfaces often have an attached pen or stylus for the purchaser to use to sign his/her name. This pen or stylus can be just as contaminated as the user interface.

Therefore, according to various embodiments of this disclosure, a handheld UV disinfectant unit is provided. The handheld UV disinfectant unit doubles as a writing tool as well, having one or more writing instruments integrated therein. This provides a multi-use, handheld tool for every-day applications that allow the consumer to disinfect a surface which will soon be touched by the user, as well as selectively use the user's own writing instrument from the same packaged unit. In some embodiments, the writing instrument can conveniently retract into the housing of the unit, concealing itself from the environment to reduce the chance of damage on the writing instrument or surrounding materials that might otherwise snag or catch on the writing instrument.

The Figures illustrate one exemplary embodiment of such a handheld UV disinfectant unit 10. The handheld UV disinfectant unit 10 is a multi-purpose device: it serves as both a disinfecting unit with a UV light source for disinfecting surfaces, and also serves as a selectable writing unit with one or more writing instruments that can extend and retract from the unit.

Figure 4:
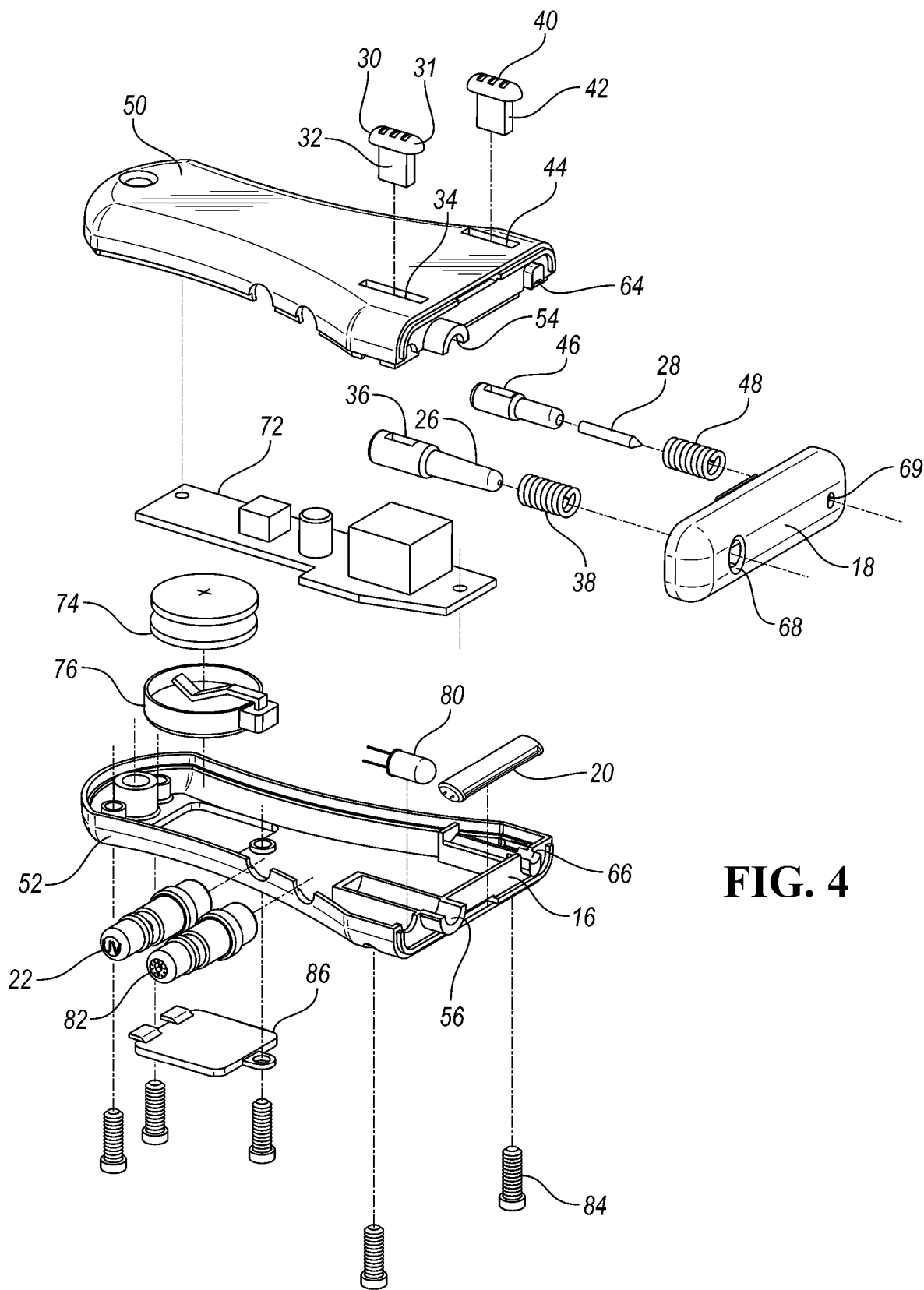
FIG. 4 is an exploded perspective view or assembly view of the handheld UV disinfectant unit of FIG. 1, according to one embodiment.

The handheld UV disinfectant unit 10 includes an outer shell or housing 12 having a first end 14 and a second end 16. A transparent lens cap 18 is removably connected to the second 16. The transparent lens cap 18 covers a UV light (e.g., cathode UV lamp) also mounted to or near the second end 16. While shielded by the lens cap 18 and not shown in FIG. 1, the UV light source is shown as element 20 in FIG. 4 described below.

By pressing a UV button 22 extending through a side surface of the housing 12, the UV light 20 is activated. With the UV light 20 on, a user can simply swipe the unit 10 across an underlying surface to disinfect the surface. In one embodiment, the UV light 20 has a 3 volt power source with a UV strength of at least 230 μW/cm. This provides a UV light that can disinfect up to 90% of the underlying surface with 1 minute of use time.

The handheld UV disinfectant unit 10 is also provided with at least one extendable and retractable writing instrument. In the embodiment shown in the Figures, the handheld UV disinfectant unit 10 is provided with two such writing instruments: an extendable and retractable stylus 26, and an extendable and retractable pen 28. FIGS. 2A-3B illustrate the extendibility and retractability of each writing instrument 26, 28.

To accomplish the extending and retracting of the writing instruments, a slider button is provided for each writing instrument. A first slider button 30 is provided to and coupled to the stylus 26 for selectively extending and retracting the stylus. The first slider button 30 has a protrusion 32 that extends from a larger head 31 and into an opening or slot 34 of the housing 12, and into an opening or slot 36 of the stylus 26. The protrusion 32 is sized and configured to slide linearly along the length of the slot 34 to allow the first slider button 30 to travel linearly, which correspondingly extends the stylus (as shown by the arrows in FIG. 2A) and retracts the stylus (as shown by the arrows in FIG. 2B). The stylus 26 is constrained to travel linearly through a track formed within the interior of the housing 12. For example, the housing may be a split-body housing in which the lower housing has a first track portion and the upper housing has a second track portion, and the two track portions cooperate when assembled to define a track for the stylus 26 to slide along. The track may have a stopper at one end to prevent further retraction, and the track may be open at its other end. A spring 38 may be provided about the stylus 26 and linearly situated between the lens cap 18 and the slot 36 to bias the slider button 30 to the retracted position.

A second slider button 40 is also provided to similarly extend the pen (as shown by the arrows in FIG. 3A) and retract the pen (as shown by the arrows in FIG. 3B). Similar structural features are provided, including a protrusion 42 extending through a slot 44 in the housing 12 and a slot 46 in a base that holds the pen 28. Another track formed within the interior of the housing may be provided for the pen 28. Another spring 48 may be similarly situated to bias the second slider button 40 to the retracted position.

The housing 18 is provided with two openings or apertures for the writing instruments to extend and retract through. In one embodiment, the housing 12 is a two-part housing, with a top housing 50 and a bottom housing 52. The top housing 50 is provided with a first semi-circular opening 54, and the bottom housing is provided with a second semi-circular opening 56. The two openings 54, 56 cooperate to define a first aperture in the housing 12 for the stylus to extend and retract through. Similarly, the top housing may be provided with another first opening 64 and the bottom housing may be provided with another second opening 66 that cooperate to define a second aperture in the housing 12 for the pen to extend and retract through.

The lens cap 18 may be provided with a pair of apertures such that the stylus and pen can extend and retract through both the housing 12 and the lens cap 18. For example, the lens cap may be provided with a first aperture 68 for the stylus 26 to pass through, and a second aperture 69 for the pen 28 to pass through. The first aperture 68 may be larger in diameter than the second aperture 69. In one embodiment, the two apertures 68, 69 are located on either side of the UV light 20 which is described in more detail below. This allows the stylus and pen to be extended out from the housing on either side of the UV light 20.

The UV light 20 is mounted to or near the end 16 of the housing 12. To activate the light, the UV button 22 is depressed, which sends a signal to a controller or circuitry on a printed circuit board (PCB) 72, causing a battery 74 (held in battery holder 76) to power the UV light 20. The UV light 20 then provides all of the disinfecting benefits described above.

In one embodiment, a light-emitting diode (LED) 80 or other similar visible light source is also provided. The LED 80 can be activated by depression of a light button 82, which again powers the LED 80 via the battery 74 in similar fashion. This provides the user with a visible light while trying to use the pen or stylus in a dimly lit environment, for example. The LED 80 is also mounted at or near the end 16 of the housing and is covered by the transparent lens cap 18.

Figure 5:
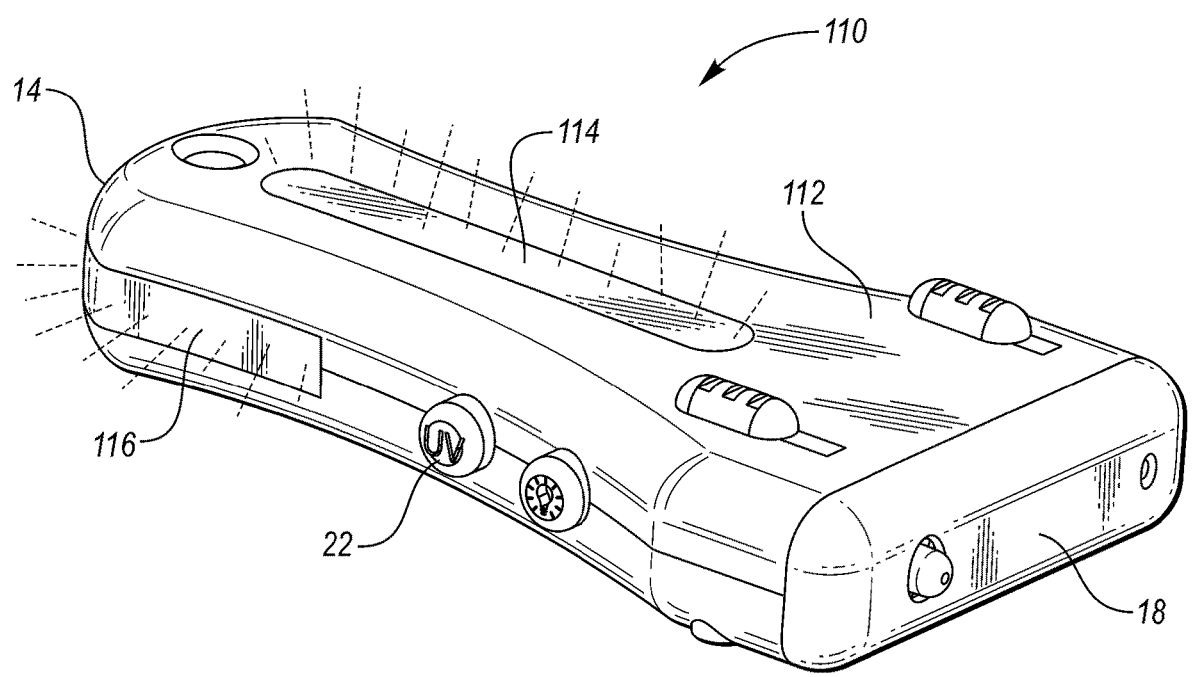
FIG. 5 is a perspective view of a handheld UV disinfectant unit according to another embodiment.

The assembly or exploded view in FIG. 5 shows where the various parts are assembled relative to other parts. A plurality of fasteners 84 can be provided to, for example, secure the two halves of the housing 12 to one another, and secure a battery door 86 to the housing to cover the battery. When assembled, a compact and handheld UV disinfectant unit with integrated writing instruments is provided.

FIG. 5 is a perspective view of an embodiment of a handheld UV light disinfectant unit 110 similar to the unit 10 described above. In this embodiment, the housing 112 includes a plurality of transparent portions 114, 116. The transparent portions may be made of glass, plastic, or other suitable materials. A second UV light (not shown) can be assembled within the interior of the handheld UV light disinfectant unit 110. The second UV light, when activated by the UV light button 22 or an additional UV light button (not shown), allows UV light to transfer through the housing at the transparent portions 114, 116. This allows a handle portion of the housing 112 to becomes a UV light disinfectant itself. This is beneficial for disinfecting the user's hands, for example, when grasping the handheld UV light disinfectant unit 110. The transparent portion 116 allows the first end 14 of the housing to also be a UV light disinfectant, which now enables both ends of the handheld UV light disinfectant unit 110 to disinfect simultaneously.

The illustrated embodiments are merely examples of the invention and not intended to be limiting to only what is shown. Redesigns and reconfigurations of parts or locations of the components are entirely within the scope of this disclosure. For example, the writing instruments may be extendable and retractable from the first end 14 of the housing rather than the second end 16. Moreover, the writing instruments may be fixedly mounted and not extendable, and a cap may be provided to cover the writing instruments. In another embodiment, the writing instruments are fixed or retractable on the sides of the unit, or between the first and second ends.

The handheld UV light disinfectant unit of the present disclosure provides advantages of being a compact, portable disinfectant, allowing a user to carry the unit even in one's own pants pocket or purse. When the user is forced to touch a user interface of other object which has been subjected to contamination from the public, the user can simply grab the handheld UV light disinfectant unit, turn on the UV light, and wave the transparent lens over the surface of the user interface or object. Then, without having to grasp onto a pen, stylus, or other writing instrument that has also been subjected to public contamination, the user can simply slide a button to extend one or more of the writing instruments out. When not in use, the writing instruments can be retracted back within the transparent lens, and while the UV light remains on, the writing instruments are disinfected due to the UV exposure. Never has such a portable multi-use tool been available for the public. The owner of such a tool is no longer forced to grasp onto multiple disinfecting units, multiple writing instruments, or rifle through a purse or container that houses more than one of these units or writing instruments, which can proliferate contamination.

It should be understood that while both a stylus and a pen are disclosed as possible writing instruments, this disclosure is not limited to only those two. Other writing instruments such as pencils, markers, etc. may be implemented into the handheld UV disinfectant unit.

The handheld UV light disinfectant unit may be powered by battery, as described above. In one embodiment, the battery can be chargeable such that the handheld UV light disinfectant unit can be plugged into a power source such as a wall plug outlet to recharge the battery.

In one embodiment, a sleeve or case may be provided to disinfect the handheld UV light disinfectant unit. The case may be a hard-cover case with a hollow cavity sized to receive the handheld UV light disinfectant unit. The interior of the case may be provided with a UV light, illuminating the interior of the case with disinfecting UV light to disinfect the outer surfaces of the handheld UV light disinfectant unit. The case may have electric circuity that enables the case to be plugged in to a power source such as a wall outlet. This allows the user to set the handheld UV light disinfectant unit in the case while the case is plugged in, and leave the handheld UV light disinfectant unit in the case for an extended period of time without fear of the disinfecting ability of the case losing power.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A handheld ultraviolet (UV) light disinfectant unit, comprising:
   a housing;
   a UV light source coupled to the housing and configured to, when activated, disinfect a surface on which UV light from the UV light source shines;
   a writing instrument coupled to the housing;
   a second writing instrument coupled to the housing adjacent to the UV light source, wherein the writing instrument is a pen and the second writing instrument is a stylus; and
   a transparent lens cap assembled over the UV light source, wherein the at least one of the pen and stylus is configured to extend and retract through the housing and the lens cap.

2. The handheld UV light disinfectant unit of claim 1, wherein both the pen and the stylus are configured to extend and retract through the housing, and at least one of the pen and stylus is configured to extend and retract at a location adjacent the UV light source.

3. The handheld UV light disinfectant unit of claim 1, further comprising a slider button extending into the housing, coupled to the at least one of the pen and stylus, and configured to slide relative to the housing to extend and retract the at least one of the pen and stylus through the housing.

4. The handheld UV light of disinfectant unit of claim 1, wherein the lens cap is removeably connected to the housing.

5. The handheld UV light disinfectant unit of claim 1, further comprising a second UV light source mounted inside of the housing, wherein at least a portion of the housing is transparent to enable UV light to transfer through the housing.

6. The handheld UV light disinfectant unit of claim 5, wherein the portion of the housing is in a location where a user's hand is placed during operation of the handheld UV light disinfectant unit.

7. The handheld UV light disinfectant unit of claim 1, wherein the housing has a first end, a second end, and a length between the first end to the second end, wherein the UV light source is mounted to or near the first end, and wherein the housing becomes smaller in a direction from the first end toward the second end.

8. A handheld ultraviolet (UV) light disinfectant unit, comprising:
- a handheld housing defining a hollow interior having a first track and a second track therein, the housing further including an end defining first and second apertures extending through the housing;
- a UV light source mounted to or near the end and configured to, when activated, disinfect a surface on which UV light shines;
- a first slider extending through the housing and into the first track, the first slider coupled to a pen to enable the pen to extend and retract through the first aperture as the first slider slides along the first track; and
- a second slider extending through the housing and into the second track, the second slider coupled to a stylus to enable the stylus to extend and retract through the second aperture as the second slider slides along the second track; and
- a transparent lens cap removably coupled to the housing, wherein the UV light source is disposed between the end and the lens cap;
- wherein the lens cap includes a first aperture aligned with the aperture of the housing and enabling the pen to extend and retract through the lens cap, and a second aperture aligned with the second aperture of the housing and enabling the stylus to extend and retract through the lens cap.

9. The handheld UV light disinfectant unit of claim 8, wherein the housing includes a pair of opposing curved side surfaces that taper inwardly in a direction away from the end, the side surfaces providing an ergonomic grip for a user's hand to grasp both side surfaces.

10. The handheld UV light disinfectant unit of claim 8, further comprising a second UV light source mounted inside of the interior of the housing, wherein at least a portion of the housing is transparent to enable UV light to transfer through the housing.

\* \* \* \* \*